(12) United States Patent
Huff et al.

(10) Patent No.: US 6,479,041 B2
(45) Date of Patent: *Nov. 12, 2002

(54) METHOD FOR PRODUCING AQUEOUS EMULSIONS OR SUSPENSIONS

(75) Inventors: Rainer Huff, Huenfeld; Gerd Frauenrieder, Rothenkirchen; Bernhard Bieber, Huenfeld, all of (DE)

(73) Assignee: Wella Aktiengesellschaft, Darmstadt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/486,506
(22) PCT Filed: Jul. 2, 1999
(86) PCT No.: PCT/EP99/04589
§ 371 (c)(1), (2), (4) Date: Feb. 28, 2000
(87) PCT Pub. No.: WO00/01474
PCT Pub. Date: Jan. 13, 2000

(65) Prior Publication Data
US 2002/0110533 A1 Aug. 15, 2002

(30) Foreign Application Priority Data
Jul. 2, 1998 (DE) .......................... 198 29 647

(51) Int. Cl.⁷ .............................. A61K 7/06; A61K 7/00
(52) U.S. Cl. .................... 424/70.1; 424/70.6; 424/401; 514/927; 514/938
(58) Field of Search ................ 424/401, 70.1, 424/70.6; 514/937, 938

(56) References Cited

U.S. PATENT DOCUMENTS

| 2,641,453 A | | 6/1953 | Teale |
| 3,791,984 A | * | 2/1974 | Brogli et al. |
| 4,463,165 A | * | 7/1984 | Engelhardt et al. |

(List continued on next page.)

FOREIGN PATENT DOCUMENTS

| DE | 808 041 | 7/1949 |
| DE | 20 04 143 A | 8/1971 |
| DE | 29 31 782 A | 2/1980 |

(List continued on next page.)

OTHER PUBLICATIONS

Andreas Domsch "Die Kosmetischen Praeparate", Band III, Lipidhaltige und Emulgierte Formulierungen, 4. Auflage Des Von G.A. Nowak Begruendeten Werkes, pp. 305–307. (1994).

(List continued on next page.)

Primary Examiner—Thurman K. Page
Assistant Examiner—Brian K. Seidleck
(74) Attorney, Agent, or Firm—Michael J. Striker

(57) ABSTRACT

A method for producing aqueous emulsions or suspensions is described, in which a liquid phase is added to a supply tank, which is connected to a homogenizer having a stator, a rotor mounted rotatably in the stator and an additional connection, through which a second phase, which is to be homogenized, can be added directly onto the rotor and comes into contact with the previously added phase only in the toothed rings of the rotor, the homogenizer is started and subsequently the second phase, which is insoluble in the previously added phase and is to be homogenized, is supplied in liquid form through the additional connection. At least one of the two phases is an aqueous phase and at least one of the two phases is not heated.

17 Claims, 2 Drawing Sheets

U.S. PATENT DOCUMENTS

| | | | |
|---|---|---|---|
| 5,366,288 A | | 11/1994 | Dahlloef |
| 5,590,961 A | | 1/1997 | Rasmussen |
| 5,607,666 A | * | 3/1997 | Masson et al. |
| 6,063,954 A | * | 5/2000 | Diener et al. |

FOREIGN PATENT DOCUMENTS

| | | |
|---|---|---|
| DE | 84 28 385.8 | 3/1985 |
| DE | 82 30 048 U | 10/1991 |
| EP | 0 801 974 A1 | 10/1997 |
| GB | 405 503 A | 2/1934 |
| WO | 94 13395 A | 6/1994 |
| WO | 95/13787 | 5/1995 |
| WO | 96 22830 A | 8/1996 |

OTHER PUBLICATIONS

Bernd Ziokowski "Mischer zur Herstellung Von Badepraeparaten und Emulsionen", Sefen–Ole–Fette–Wachse—112 JG, NR. 15, 1986, pp. 532–536.

"Technologische Aspekte Bei der Herstellung Von Emulsionene" by W. Skrypzak et al, SOFW–Journal, 118. Jahrgang, 5/92, pp. 287–296.

"Moderne Verfahrung zur Herstellung Von Halbfesten und . . . " by Kutz et al, SOFW–Journal, 124. Jahrgang 5/98, pp. 308–313.

Remington's Pharmaceutical Sciences, 18th Ed., Chapter 83, Emulsions. (1990).*

* cited by examiner

METHOD FOR PRODUCING AQUEOUS EMULSIONS OR SUSPENSIONS

This application is a 371 of PCT/EP99/04589, field Jul. 2, 1999

BACKGROUND OF THE INVENTION

1. Field of the Invention

The present invention relates to a method of making aqueous emulsions or suspensions and, more particularly, to a method of making aqueous emulsion or suspensions with a homogenizer of the rotor/stator type.

2. Description of the Related Art

Disperse preparations of the emulsion or suspension type play a prominent role in the preparation of cosmetics, pharmaceutical products and foods. The optimization of the production process, especially with regard to saving time and energy, is therefore of particular importance. A review of modern methods of producing semisolid and liquid emulsions is given in the article in SÖFW-Journal, volume 124, 5/98, pages 308 to 313, as well as in the article in S ÖFW-Journal, volume 118, 5/92, pages 287 to 296. With regard to the temperatures at which they are carried out, the methods can be divided into hot/hot, hot/cold and cold/cold methods.

The standard method of preparing emulsions is the hot/hot method, in which the fatty phase is heated to about 75° C. and combined with the water phase, which has also been heated to about 75° C. Subsequently, the excess energy, which was supplied in the form of heat, is removed with the expenditure of much time. This method is therefore very time-consuming and cost-intensive.

In order to reduce the energy consumption and shorten the production time, so-called hot/cold and cold/cold methods have been developed. However, these methods have the disadvantage that they are tied to certain conditions and their applicability is therefore very limited and not usable for all emulsions and dispersions. For the hot/cold method, for example, the hot oil phase is added to the emulsifying tank and water, which has not been heated, is emulsified into the hot oil phase. Until now, the prerequisites for this method were a very slow addition of water to avoid crystallization by shock cooling, as well as a sufficiently high proportion of fat to prevent a drop in temperature to below the solidification point during the addition of water. This method therefore is still time consuming and, moreover, limited to emulsions with a high fat content.

The WO 95/13787 discloses that, for producing emulsions, it is possible to mix the fatty phase and the aqueous phase at ambient temperature, however, only under the condition that, first of all, a suitable emulsifier is present and, secondly, that the fatty phase is an oil of moderate polarity. For emulsifying oils with a high or low polarity at room temperature, it is necessary that additional metal soaps be present. To begin with, these metal soaps must be dissolved in the oil at elevated temperatures and subsequently cooled; this is also time-consuming and cost-intensive.

Emulsions or suspensions, produced by conventional methods, frequently also have the disadvantage that the emulsified or suspended particles have a particle size, which is not uniform enough or too large. This is associated with an effective surface area, which is too small for many applications. Moreover, the emulsion or suspension is not dispersed optimally.

SUMMARY OF THE INVENTION

It was therefore an object of the invention to make available a simplified, broadly applicable method for producing suspensions or emulsions, which is not time-consuming and cost-intensive and, at the same time, not subject to the limitations named above and does not adversely affect significantly or even improves the desired properties of the product produced.

This objective is accomplished by a method of making aqueous emulsions or suspensions, wherein (A) a liquid phase is first added to a tank, the latter being connected to a homogenizer, which is of the rotor/stator type and has an additional connection, through which a phase, which is to be homogenized, can be added directly onto the rotor and comes into contact with the previously added phase only in the toothed rings of the homogenizer, (B) the homogenizer is started and subsequently (C) a second phase, which is insoluble in the previously added phase and is to be homogenized, is supplied in liquid form over the additional connection of the homogenizer, at least one of the two phases being an aqueous phase and at least one of the two phases not being heated.

The aqueous phase can either be added first, in which case the water-insoluble phase is supplied over the additional connection of the homogenizer, or the aqueous phase is supplied to a water-insoluble phase, which has been added previously to the tank.

The concept, "aqueous phase", comprises water as well as mixtures of water with water-soluble solvents, such as low molecular weight alcohols, for example, ethanol or isopropanol or polyols, such as ethylene glycol, diethylene glycol, butylene glycol or glycerin.

The particles, which are to be homogenized, have an optimum particle size of, for example, about 1 μm, an optimum distribution in the external phase and a large effective surface. Consequently, raw material savings can be realized since the substance, which is to be homogenized, can be used in lesser amounts. The problem of the undesired crystallization processes also no longer arises.

If the phase, which is to be homogenized, exists in solid form at room temperature, it is added in the molten state. Such phases are waxes or wax-like materials, such as natural waxes, which can be regenerated (insect wax, animal wax and plant wax), fossil waxes (crude oil wax, brown coal wax, peat wax or ozokerites), synthetic waxes (Fischer-Tropsch wax, polyethylene wax or amide wax), higher melting paraffins, esters, fats, long-chain carboxylic acids or long-chain alcohols, each having a melting or solidifying point above room temperature.

The temperatures of the previously added phase and of the melt supplied ideally are selected so that the resulting temperature of the mixture is below the crystallization or solidification point of the substance, which is to be homogenized into the previously added phase. For example, if the temperature of the molten wax is 70° to 90° C. and the temperature of the previously added aqueous phase is 10° to 25° C., a mixture with a temperature between 10° and 40° C. can be attained. The wax suspension obtained can then immediately afterwards be filled into containers, ready for use, without the need for a subsequent protracted cooling and without the danger of a subsequent time-delayed change in the viscosity or consistency, since the crystallization effects are concluded immediately.

In a special embodiment, the phase, which is to be homogenized, especially a molten wax or a melt of a substance, which has a wax-like consistency at room temperature, is homogenized without an emulsifier.

If the phase, which is to be homogenized, is a liquid at room temperature, it is preferably added without being heated. Such a phase may be an oil or an oil-like material, such as naturally occurring oils (vegetable or animal fatty oils), which can be regenerated, synthetic oils, silicone oils, mineral oils, essential oils, water-insoluble, branched or linear aliphatic hydrocarbons, linear or branched alcohols, especially fatty alcohols as well as long-chain ethers or esters. Suitable hydrocarbons are, for example, liquid paraffins, squalane or squalane. Furthermore, esters of trihydric and multihydric alcohols, especially vegetable triglycerides, such as olive oil, almond oil, peanut oil, sunflower oil as well as synthetic triglycerides, such as $C_8$ to $C_{10}$ fatty acid triglycerides or also jojoba oil, are suitable.

Furthermore, monoesters or diesters of the formula $R^1$—$COOR^2$, $R^1$—$COO$-$R^3$—$OOCR^1$ and $R^2COO$-$R^3$—$OOCR^2$, in which $R^1$ represents a $C_8$ to $C_{22}$ alkyl group, $R^2$ a $C_3$ to $C_{22}$ alkyl group and $R^3$ a $C_2$ to $C_{16}$ alkylene group, are suitable as substance, which is to be homogenized. Naturally occurring monoester mixtures and wax ester mixtures, such as those present in jojoba oil or sperm oils, and branched primary alcohols, such as those known under the name of Guerbetal alcohols, are also suitable.

In addition, materials, which are usually used as opacifying agents in cosmetic materials, are suitable as substances, which are to be homogenized. These are, in particular, those having the formula $R^1$—$COO$—$(CHR^4CHR^5O)_n$—$COR^6$, wherein $R^1$ represents a $C_8$ to $C_{22}$ alkyl group, $R^4$ and $R^5$ represent hydrogen or methyl and $R^6$ represents hydrogen or $R^1$ and n is a number between 1 and 12 and preferably 1, 2, 3 or 4. Diesters of glycol and fatty acids are preferred.

If the hydrophobic substance, which is to be homogenized, is a liquid at room temperature, it is particularly advantageous and saves time and energy, if neither of the phases is heated (cold/cold emulsification). A special embodiment of the invention therefore is a method for producing aqueous emulsions or suspensions of hydrophobic materials, which are liquid at room temperature, for which method (A) a liquid phase is added to a tank, the latter being connected to a homogenizer of the rotor/stator type and having an additional connection, through which a phase, which is to be homogenized, can be added directly onto the rotor and comes into contact with the previously added phase only in the toothed rings of the homogenizer, and subsequently (B) a second phase, which is insoluble in the previously added phase and is to be homogenized, is supplied in liquid form over the additional connection of the homogenizer, one of the two phases being an aqueous phase and the other phase a hydrophobic phase and neither of the two phases being heated.

The amount of substance to be homogenized, as a proportion of the finished emulsion or suspension, depends on the requirements of the end product that is to be produced. For example, for the treatment of hair, it may amount to 2 to 10% by weight or, for creams, such as hair dyes, it may even amount to about 50% by weight The homogenizer, which is to be used, is an essential part of the method. It is of the rotor/stator type and has an additional connection at a very specific position. Conventional, rotor/stator homogenizers are described, for example, in Andreas Domsch, "Die kosmetischen Präparate" (The Cosmetic Preparations), volume III, 4th edition, pages 305 to 307, as well as in the article in Seifen-Öle-Fette-Wachse, volume 112, 1986, pages 532 to 536. The rotor stator principle is the most frequently employed homogenizing method for making cosmetic preparations. For this method, the material, which is to be homogenized, is moved by means of a rotating part, the rotor, through a stationary part, the stator. Between the rotor and the stator, there is only an extremely small gap. The homogenization effect is based on the turbulences occurring in the shear gap. When conventional homogenizers are used without an additional connection, the substance to be homogenized is already in contact with the aqueous phase and is thus present as a pre-mixture or a pre-emulsion. With these conventional homogenizers, emulsions can be produced only according to the conventional methods, but not according to the inventive method. According to the inventive method, contact between the substance to be homogenized and the previously added phase before the actual homogenization is to be avoided.

BRIEF DESCRIPTION OF THE DRAWING

The objects, features and advantages of the inventive method will now be described in further detail with the aid of the following figures in which.

Figure 1:
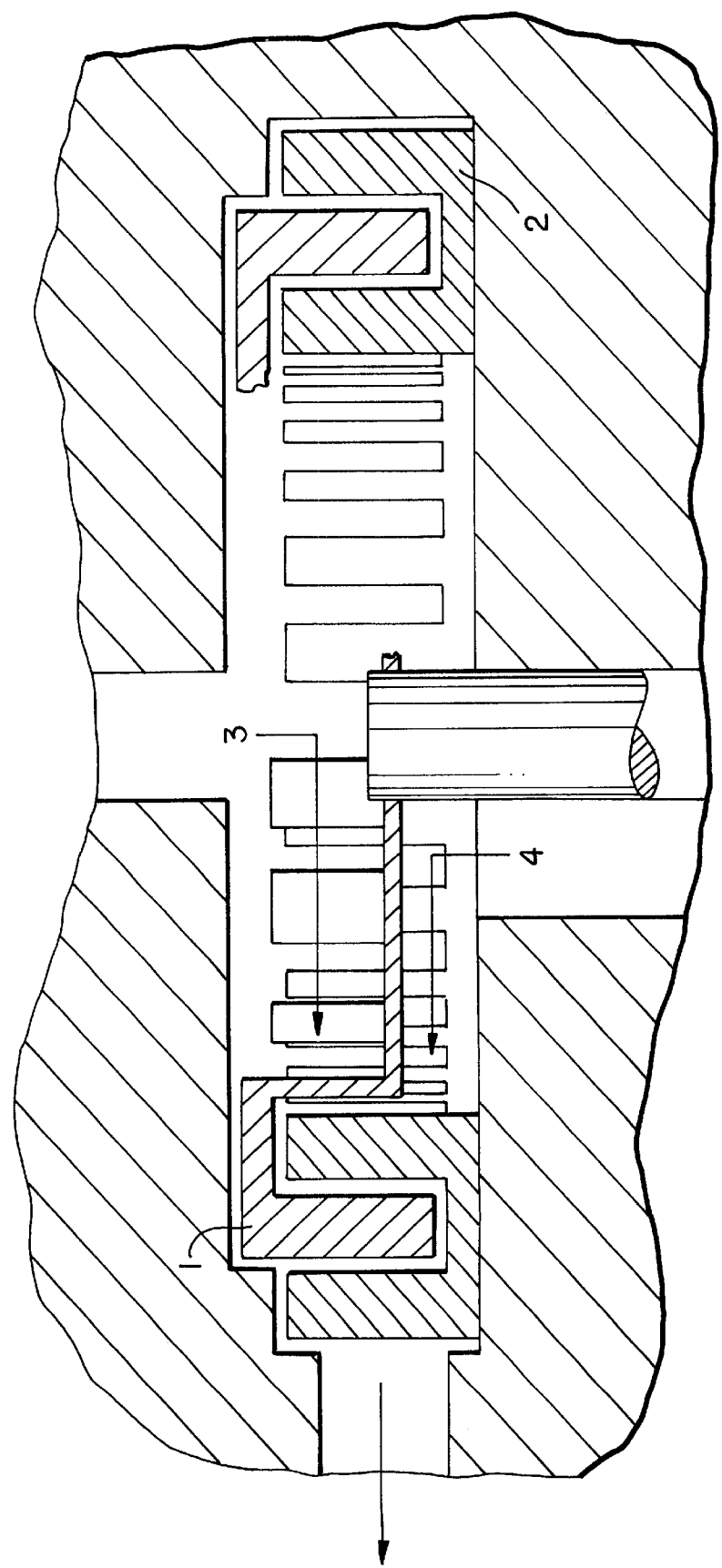
FIG. 1 is a cross-sectional view through a suitable homogenizer of the rotor/stator type used in the method according to the invention in the vicinity of the toothed rings of the rotor.

A suitable homogenizer, with a rotor (1) and a stator (2), is shown in FIG. 1. Only in the toothed rings does the phase (3), which was added previously, come into contact with the second phase (4), which is to be homogenized. The finished product (5) emerges in the form of a fine dispersion.

A further object of the invention is the use of a homogenizer of the rotor/stator type, which has an additional connection, through which a substance, which is to be homogenized, can be added directly to the rotor and the substance comes into contact with the external, aqueous phase only in the toothed rings of the homogenizer, for the purpose of producing suspensions of molten wax or molten wax-like materials and water, which have not been heated, or for producing emulsions of hydrophobic substances, which are liquid at room temperature and have not been heated, and water, which has not been heated. In particular, lotions, creams and ointments, or cosmetic materials and foods or pharmaceutical agents in emulsion form can advantageously be produced. Cosmetic materials in emulsion form are, for example, hair or skin care agents, such as hair care agents, agents for the treatment of hair, hair dyes, skin creams or sunscreens. Foods in emulsion form are, for example, sauces, mayonnaises, creamy sandwich spreads, emulsified salad dressings or margarine.

Attempts were made to emulsify at room temperature, the substance to be homogenized being supplied over an additional connection to the inlet of the homogenizer, the additional connection being positioned directly in front of the rotor/stator unit. These attempts did not lead to a satisfactory result since, before the actual homogenization process, there still is contact here, even if only a very brief one, between the substance to be homogenized and the external phase. Presumably, there is gelling, lump formation or the precipitate formation, which produces a coarser emulsion or requires a longer mixing time and, in the extreme case, can even lead to the blockage of the rotor. Pursuant to the invention, therefore, the homogenizer must have an additional connection, which is positioned, so that the substance, which is to be homogenized, reaches the toothed ring of the rotor/stator directly without previously coming into contact with the remaining external phase. In principle, any conventional, commercial homogenizer can be used, provided that it is changed structurally in the manner described. A particularly suitable homogenizer is offered, for example, by Firma Berents under the name of Becomix Duo-Homogenisator DH 2000.

Ideally, the ratio of the partial streams of the previously added phase, on the one hand, and the phase to be homogenized, on the other, which flow into the homogenizer, are adjusted so that the phase to be homogenized, which is supplied over the additional connection, is not transported into a region, located upstream from the toothed rings of the rotor/stator unit, where it can come into contact with the previously added phase before the homogenization. The partial stream, supplying the phase to be homogenized, can be adjusted by applying a pressure difference. Preferably, a slightly reduced pressure of, for example, 0.2 to 0.8 bar and preferably of 0.3 to 0.6 bar is applied. The partial stream, supplying the previously added phase, can be adjusted by adjusting the peripheral speed of the rotor. For typical, conventional, commercial rotors, the peripheral speed is, for example, 20 to 40 m/s and preferably 25 to 30 m/s.

The homogenization can be carried out without an emulsifier However, an emulsifier or a surfactant, as emulsifier, may also be present and preferably is introduced before the substance, which is to be homogenized, was supplied over the additional connection of the homogenizer. The emulsifier may be present in amounts of 0.5 to 30% by weight of the finished composition.

Nonionic, anionic, cationic, amphoteric or zwitterionic emulsifiers are suitable. Suitable emulsifiers are listed, for example, in the "International Cosmetic Ingredient Dictionary and Handbook", 7th edition, volume 2, in the "Surfactants" section and especially in the "Surfactants—Emulsifier Agents".

Nonionic emulsifier are, for example, ethoxylated fatty alcohols, ethoxylated nonylphenols, monoglycerides and diglycerides of fatty acids, ethoxylated castor oil and ethoxylated, hydrogenated castor oil, fatty acid alkanolamides and ethoxylated fatty esters. Cationic emulsifiers are, for example, long-chain quaternary ammonium compounds such as those known under the CTFA name of "quaternium", for example, alkyltrimethylammonium salts of dialkyldimethylammonium salts with $C_8$ to $C_{22}$ alkyl groups. Anionic emulsifiers are, for example, fatty alcohol sulfates, alkyl ether sulfates and alkylbenzenesulfonates. Amphoteric emulsifiers are, for example, the different known betaines, such as fatty acid amidoalkylbetaines and sulfobetaines and $C^8$ to $C_{22}$ alkyl betaines.

The inventive method is particularly suitable for producing an opacifier composition for cosmetic materials. For this purpose, initially a concentrated alkyl ether sulfate, such as lauryl ether sulfate, is dissolved using the homogenizer, into which electrolyte-free water, which had not been heated, had previously been placed. Subsequently, a water-insoluble opacifying agent, such as a diester of ethylene glycol and fatty acid or of polyethylene glycol and fatty acid, for example, polyethylene glycol (3)-distearate, is homogenized in the liquid or molten state in the water.

The inventive method is especially suitable for producing cosmetic and pharmaceutical materials. In this case, either the active or inactive cosmetic materials are contained in the previously added phase and the emulsion or suspension is formed subsequently by the inventive method or the emulsion or suspension is produced first and the cosmetic or pharmaceutical active or inactive ingredients are introduced subsequently. Since the emulsion or suspension, primarily produced pursuant to the invention, is extremely fine and has a low viscosity, the further active and inactive ingredients can be incorporated significantly more easily and quickly than they can according to conventional methods, as a result of which the formulation times are clearly shortened.

It is also particularly advantageous to produce hair dyeing creams according to the inventive method, particularly hair dyeing creams for oxidizing hair dyes containing dye intermediates, which respond to oxidation. These hair dyeing creams are usually based on a wax-containing cream. With conventional methods of production, a hydrophobic, molten wax phase, heated to about 70° to 80° C., is emulsified at a temperature of 70° to 80° C. in an aqueous phase, containing the dye intermediates as well as any additional conventional additives. Subsequently, the emulsion must be cooled very slowly and with delay and stirring, in order to prevent uncontrolled crystallization of the wax (formation of wax specks). During this relatively long cooling, undesirable oxidation reactions may occur as a result of the oxygen stirred in from the air. In addition, there may be post-thickening, which may cause difficulties when filling the finished product into containers.

The disadvantages of the conventional method of emulsifying hot are overcome by the inventive method. Time-consuming and energy-consuming heating and cooling of the whole composition are not required. The danger of forming specks and of undesirable oxidation reactions is clearly reduced. Immediately after the wax phase is supplied, the dye composition obtained can be filled, as finished product, into containers without any further homogenizing steps, since cooling is not required and the consistency does not change due to post-thickening. Because of the much finer dispersion of the hydrophobic phase, a significantly larger specific surface area and, with that, a higher effectiveness of the raw materials is attained. As a result, clearly less raw materials can be used, the savings being about 10 to 30% relative to cream compositions produced by conventional means.

The object of the invention therefore especially is a method for producing a hair dye cream, for which (A) hair dyes or dye intermediates and optionally further conventional additives are added to water, which has not been heated, in a tank, the latter being connected to a homogenizer of the rotor/stator type and having an additional connection, through which a phase, which is to be homogenized, can be added directly onto the rotor and comes into contact with the previously added phase only in the toothed rings of the homogenizer, (B) the homogenizer is started, (C) a melt of a substance, which is wax-like at room temperature, optionally with further, conventional hydrophobic additives, dissolved therein, is supplied over the additional connection of the homogenizer and by these means is homogenized in the previously added aqueous phase.

Ideally, the temperature of the previously added aqueous phase is selected so that the temperature of the mixture, which results after the wax melt is emulsified, is lower than the solidification point of the wax. If the temperature of the molten wax is, for example, 70° to 90° C. and the temperature of the previously added aqueous phase is 10° to 25° C., a mixture temperature can be reached, which is between 20° and 40° C. The dye cream can be filled into containers directly afterwards and is ready for use.

If the end product is a viscous composition, the desired final viscosity, especially in the case of O/W emulsions, frequently is obtained already by the homogenization. However, the desired final viscosity can also be adjusted (preferably at the end of the manufacturing process) by the addition of an electrolyte, such as sodium chloride, or of a different, thickening material, such as celluloses or cellulose derivatives.

Compositions, produced by conventional methods, frequently show the effect of post-thickening, which means that the final viscosity and consistency are developed only after a certain period of time. Compositions, produced by the inventive method, do not have this disadvantage. Instead, they have their final viscosity already immediately at the conclusion of the manufacturing process.

Compositions, prepared by conventional methods, frequently show the effect of a viscosity change under pressure or, when stressed mechanically. This becomes noticeable in a negative way especially when filling the products into containers with pumps or may even prevent a transfer from one container to another with conventional pumps. Compositions, prepared by the inventive method, do not have this disadvantage. They are not sensitive to pressure and can be pumped without problems with conventional pumps and filled into containers.

Figure 2:
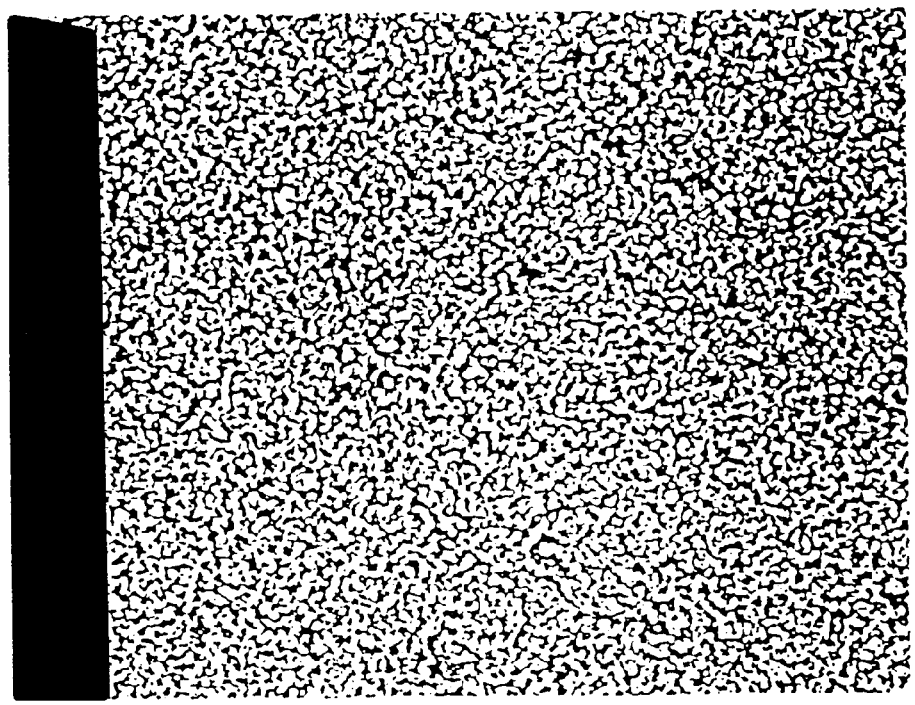
FIG. 2 is a photographic representation of a dispersion produced by a method not according to the invention.
Figure 3:
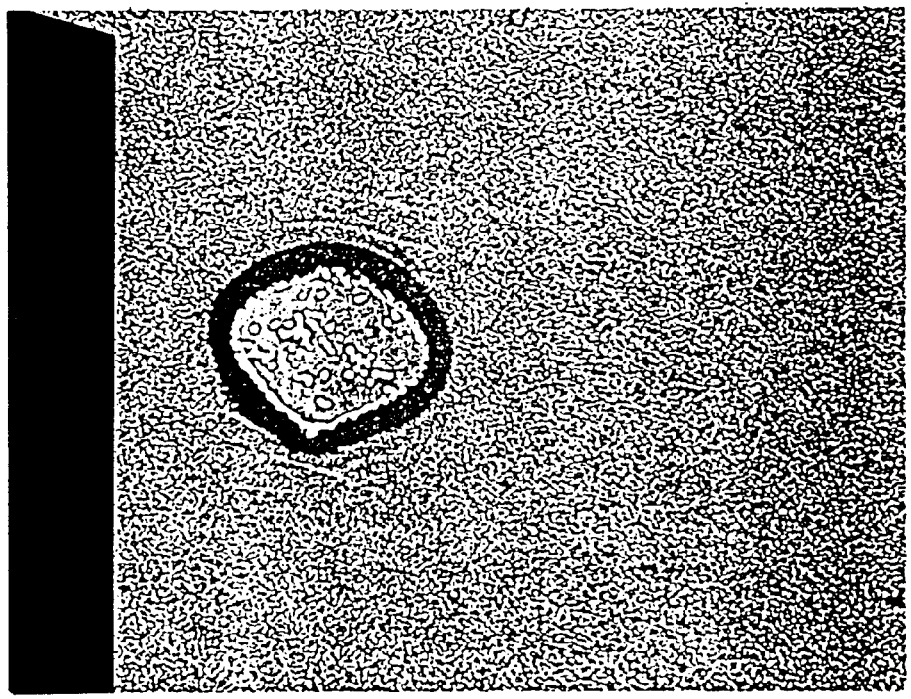
FIG. 3 is a photographic representation of a dispersion produced by a method according to example 1 of the invention.

It has been observed that, compared to suspensions or emulsions produced by conventional means, the emulsions or suspensions produced pursuant to the invention, at the same concentration and using the same amount of hydrophobic materials, have advantageous properties. Physically, this is observed in a higher viscosity of the compositions produced pursuant to the invention. However, the application properties of the products are also improved. For example, for a hair care material, in the form of a pumpable foam, it was found that the feel and combability of the treated hair are better and the foam is creamier and softer than in the case of a product, not produced pursuant to the invention but having the identical chemical composition. The improved consistency properties and application properties presumably are attributable to a better, finer dispersion of the internal phase or to a smaller particle diameter of the dispersed phase, as shown by a comparison of FIGS. 2 and 3. FIG. 3 shows a dispersion, produced pursuant to the invention as in Example 1. FIG. 2 shows a dispersion of the same chemical composition, not produced pursuant to the invention and having a distinctly finer and more uniform distribution of the dispersed phase. Therefore, aqueous emulsions or suspensions, which are produced according to the inventive method, are also an object of the invention. The particle diameter of the dispersed phase preferably is smaller than 1 $\mu$m and preferably smaller than 0.2 $\mu$m.

The concept of "not heated" is defined in this application to mean that a material or mixture of materials is not brought to a temperature above ambient by supplying heat energy and, instead, is present at a temperature at or below ambient.

EXAMPLES

Example 1

Preparation of an Opacifier Concentrate

Water (113 L) and 450 g of citric acid were added at a temperature of 13.5° C. to a kettle, to which a homogenizer of the Becomix Duo-Homogenisator DH 2000 type (Berents GmbH & Co. KG) was connected. With the help of a pump, 18 kg of 70% lauryl ether sulfate were introduced into the water over the additional connection of the homogenizer, the temperature being 15° C. Subsequently, a melt of polyethylene glycol (3)-distearate, heated to 86° C., was introduced into the aqueous surfactant solution over the additional connection of the homogenizer. The temperature of the mixture after the introduction was 27.5° C. A further 18 kg of 70% lauryl ether sulfate was homogenized in two steps over the additional connection of the homogenizer. It is, however, also possible to incorporate the whole amount of surfactant into the water at the beginning. The final temperature of the emulsion was 36° C.

The composition obtained has a low viscosity of 140 mPa (according to MV-DIN/7) and is very homogeneous. The composition was,subjected to a load test in a centrifuge at 2000 rpm. After being subjected to these conditions for 5 minutes, the composition showed no symptoms of separation. FIG. 3 shows an enlarged photographic representation of the dispersion obtained. (The circular shape represents an inclusion of an air bubble.) The size of the dispersed particles is smaller than or equal to 0.2 $\mu$m.

The final viscosity is set with sodium chloride. The composition obtained is suitable for use as an opacifier for the production of shampoos.

Comparison Example 1

Conventionally Produced Opacifier Concentrate

FIG. 2 shows an enlarged photographic representation of a dispersion of the same chemical composition as that of Example 1, but produced by conventional means. The magnification is the same as that for the inventive dispersion of FIG. 3. The size of the dispersed particles is greater than or equal to 1 $\mu$m.

Example 2

Preparation of an Emulsifier-Containing Wax Suspension in Water

Water (95 kg) and 8 kg of a 25% solution of cetyltrimethylammonium chloride was added at a temperature of 12° C. to a kettle, to which a homogenizer of the Becomix Duo-Homogenisator DH 2000 type (Berents GmbH & Co. KG) was connected. Liquid cetylaryl alcohol (5 kg), heated to 65° C., was introduced into the water previously added to the kettle over the additional connection of the homogenizer, a vacuum of 0.4 bar being applied. Subsequently, the mixture was cycled through the homogenizer for a further 5 minutes. A homogeneous, highly viscous composition resulted.

A comparison with an emulsion, produced in the conventional way, showed that, because of the fine dispersion of the raw materials, savings of at least 50% of the raw materials are possible with the inventive method. A dilution of the composition, produced pursuant to the invention, in the ratio of 1:1 with water, results in a usable, homogeneous emulsion with a viscosity of 520 mPas at 25° C.

Example 3

Preparation of a Basic Cream Composition

Water (106 kg) was added cold (19° C.) to a kettle with stirrer, to which a homogenizer of the Becomix Duo-Homogenisator DH 2000 type (Berents GmbH & Co. KG)

was connected. Over the additional connection of the homogenizer, 8 kg of a 70% sodium lauryl ether sulfate was introduced into the water, which had previously been added to the kettle. For this purpose, a vacuum was applied. A 25% aqueous solution (11.1 kg) of alkyl sulfates (Texapon KE 2510 of Firma Kenkel KGaA) was added to the formulation from above with stirring. A mixture of 10.12 kg of glyceryl stearate, 3.68 kg of lanolin alcohol, 4 kg of glycol distearate and 28.98 kg of cetylaryl alcohol was melted at 85° C. and added over the additional connection of the homogenizer, a vacuum having been applied. A homogeneous, viscous cream was formed.

Example 4

Preparation of a Hair Dye Cream for Oxidation Hair Dyes

Water (80 kg) was added cold (15° C.) to a kettle with stirrer, to which a Becomix Duo-Homogenisator DH 2000 type (Berents GmbH & Co. KG) was connected. Over the additional connection of the homogenizer, 8 kg of 70% sodium lauryl ether sulfate was introduced into the water, which had been previously added to the kettle, a vacuum having been applied. Subsequently, the dye intermediates as well as the further, conventional hydrophilic inactive and additional materials were added to the formulation from above with stirring.

A mixture of 10.5 kg of glyceryl stearate, 3.8 kg of lanolin alcohol, 0.85 kg of glycol distearate and 30 kg of cetylaryl alcohol were melted at 77° C. and added over the additional connection of the homogenizer, a vacuum of 0.3 bar having been applied and the peripheral speed of the homogenizer being 28 m/s. The mixing temperature was 37° C. A homogeneous, viscous composition without wax or dye specks was formed, which could be filled into containers immediately afterwards.

What is claimed is:

1. A method for producing aqueous emulsions or suspensions, wherein
   (A) a liquid phase is added to a tank, the latter being connected to a homogenizer of the rotor/stator type, said homogenizer having an additional connection, through which a phase, which is to be homogenized, is added directly onto the rotor and comes into contact with the previously added phase only in the toothed rings of the homogenizer,
   (B) the homogenizer is started and subsequently
   (C) a second phase, which is insoluble in the previously added phase and is to be homogenized, is supplied in liquid form over the additional connection of the homogenizer,
      at least one of the two phases being an aqueous phase and one of the two phases not being heated.

2. The method of claim 1, wherein the phase previously added to the kettle is aqueous.

3. The method of claim 1, wherein the phase subsequently supplied is aqueous.

4. The method of claim 1 wherein the phase, which is to be homogenized, is solid at room temperature and supplied in the molten state.

5. The method of claim 4, wherein the phase, which is to be homogenized, is a molten wax.

6. A method for producing a suspension of claim 5, wherein the molten wax is introduced without an emulsifier into water at ambient temperature.

7. The method of claim 1, wherein the phase, which is to be homogenized, is liquid at room temperature and supplied without being heated.

8. A method for producing aqueous emulsions or suspensions, in which a liquid phase is added to a supply tank, said supply tank is connected to a homogenizer, said homogenizer has a stator, a rotor mounted rotatably in the stator and an additional connection, through which a second phase, which is to be homogenized, is added directly onto the rotor and comes into contact with a previously added phase only in the toothed rings of the rotor; the homogenizer is started and subsequently said second phase, which is insoluble in the previously added phase and is to be homogenized, is supplied in liquid form through the additional connection, at least one of the two phases being an aqueous phase and at least one of the two phases being not heated, wherein an emulsifier or a surfactant is introduced over the additional connection to the homogenizer before the second phase, which is to be homogenized, is supplied.

9. A method for producing an opacifier composition, for which
   (A) water, which has not been heated, is added to a tank, the latter being connected to a homogenizer of the rotor/stator type, said homogenizer having an additional connection, through which a phase, which is to be homogenized, is added directly onto the rotor and comes into contact with the previously added phase only In the toothed rings of the homogenizer,
   (B) the homogenizer is started and subsequently
   (C) an alkyl ether sulfate is supplied over the additional connection of the homogenizer and, by these means, is dissolved in the water and
   (D) an opacifier in liquid form is supplied over the additional connection of the homogenizer and homogenized by these means in the surfactant solution.

10. A method for producing a hair dye cream, wherein
   (A) a hair dye or a dye intermediate and optionally additional conventional additives are added to water at room temperature in a container, a homogenizer of the rotor/stator type being connected to the tank and having an additional connection, through which a phase, which is to be homogenized, is added directly onto the rotor and comes into contact with the previously added phase only in the toothed rings of the homogenizer,
   (B) the homogenizer is started,
   (C) a melt of a wax-like substance, optionally with further, conventional, hydrophobic additives, dissolved therein, is supplied over the additional connection of the homogenizer and homogenized by these means in the aqueous phase in the container.

11. A method for producing a cosmetic or pharmaceutical composition according to claim 1, 8 or 9, and further comprising adding cosmetic active ingredients and additives in the previously added phase and then producing the emulsion or suspension, or further comprising producing the emulsion or suspension first and then adding cosmetic or pharmaceutical materials to the emulsion or suspension; and subsequently adding thickening materials to the cosmetic or pharmaceutical composition thus formed in order to adjust a viscosity thereof.

12. The method of claim 1, wherein the ratio of the partial stream, supplying the phase to be homogenized, to the partial stream, supplying the previously added phase, is selected so that the phase to be homogenized is not transported into a region, upstream from the toothed rings of the rotor/stator unit, where it can come into contact with the previously added phase before the homogenization.

13. The method of claim 12, wherein the partial stream, supplying the phase to be homogenized, is adjusted by applying a pressure difference and the partial stream, supplying the previously added phase, is adjusted by adjusting the circumferential speed of the rotor.

14. If The method of claim 13, wherein the substance, to be homogenized, is a hydrophobic substance, which is solid or wax-like at room temperature and is supplied in a molten state and wherein the temperatures of the phase, previously added, and of the melt supplied are selected, so that the resulting temperature of the mixture is below the crystallization or solidification point of the substance, which is to be homogenized.

15. A method for producing aqueous emulsions or suspensions of hydrophobic materials, which are liquid at room temperature, wherein (A) a liquid phase is added to a tank, the latter being connected to a homogenizer of the rotor/stator type, said homogenizer having an additional connection, through which a phase, which is to be homogenized, is added directly onto the rotor and comes into contact with the previously added phase only in the toothed rings of the homogenizer, (B) a second phase, which is insoluble in the previously added phase and is to be homogenized, is supplied in liquid form over the additional connection of the homogenizer, one of the two phases being an aqueous phase and neither of the two phases being heated.

16. An aqueous emulsion or suspension, produced by the method of claim 1.

17. A method of producing aqueous emulsions or suspensions, said method comprising the steps of:

a) providing an apparatus including a supply tank for a first liquid phase and a homogenizer for making an aqueous emulsion or suspension from the first liquid phase and a second liquid phase, wherein said homogenizer is connected to said supply tank and said homogenizer comprises a stator, a rotor rotatably mounted in the stator, said rotor including a toothed ring, and an additional connection to the homogenizer through which the second liquid phase is supplied to the homogenizer, said additional connection being arranged so that said second liquid phase comes into contact with said first liquid phase only in the toothed ring of the rotor;

b) adding the first liquid phase to the supply tank and supplying the first liquid phase to the homogenizer from the supply tank;

c) starting the homogenizer and subsequently;

d) supplying the second liquid phase to the homogenizer through the additional connection only so that said second liquid phase only comes into contact with said first liquid phase in the toothed ring of the rotor.

* * * * *